United States Patent
Kumar et al.

(10) Patent No.: US 11,446,472 B2
(45) Date of Patent: Sep. 20, 2022

(54) LOW-DRAG SEPTUM FOR A CATHETER SYSTEM

(71) Applicant: Becton, Dickinson and Company, Franklin Lakes, NJ (US)

(72) Inventors: Jithendra Kumar, Singapore (SG); Linda Kunardi, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 193 days.

(21) Appl. No.: 16/532,132

(22) Filed: Aug. 5, 2019

(65) Prior Publication Data

US 2020/0061343 A1   Feb. 27, 2020

Related U.S. Application Data

(60) Provisional application No. 62/722,041, filed on Aug. 23, 2018.

(51) Int. Cl.

| | | |
|---|---|---|
| *A61M 25/06* | (2006.01) | |
| *A61M 5/32* | (2006.01) | |
| *A61M 5/162* | (2006.01) | |
| *A61B 5/15* | (2006.01) | |

(Continued)

(52) U.S. Cl.
CPC .... *A61M 25/0606* (2013.01); *A61M 25/0631* (2013.01); *A61M 25/0693* (2013.01); *A61B 5/15003* (2013.01); *A61B 5/150732* (2013.01); *A61M 5/1626* (2013.01); *A61M 5/329* (2013.01); *A61M 25/0097* (2013.01); *A61M 25/065* (2013.01); *A61M 39/045* (2013.01)

(58) Field of Classification Search
CPC .... A61M 2039/0036; A61M 2039/066; A61M 2025/0018; A61M 2039/1072; A61M 2039/0633; A61M 25/0606; A61M 25/0631; A61M 25/0693; A61M 25/065; A61M 25/0097; A61M 5/392; A61M 5/1626; A61M 2039/062; A61M 2039/0081; A61B 5/15003; A61B 5/150732

See application file for complete search history.

(56) References Cited

U.S. PATENT DOCUMENTS

| | | |
|---|---|---|
| 5,401,248 A | 3/1995 | Bencini |
| 2002/0007152 A1 | 1/2002 | Hermann et al. |

(Continued)

FOREIGN PATENT DOCUMENTS

| | | |
|---|---|---|
| CN | 2889352 | 4/2007 |
| CN | 101296720 | 10/2008 |

(Continued)

*Primary Examiner* — Bhisma Mehta
*Assistant Examiner* — Neeraja Gollamudi
(74) *Attorney, Agent, or Firm* — Kirton McConkie; Whitney Blair; Kevin Stinger

(57) ABSTRACT

A peripheral intravenous catheter assembly may include a low-drag septum. The septum may include a body having a distal end and a proximal end, which may be sealed. The septum may include a slot disposed within an outer surface of the body and oriented along a longitudinal axis of the body. The slot may include a distal end spaced apart from the distal end of the body, and a proximal end spaced apart from the proximal end of the body. An introducer needle may extend through the slot.

17 Claims, 16 Drawing Sheets

(51) Int. Cl.
*A61M 39/04* (2006.01)
*A61M 25/00* (2006.01)

(56) References Cited

U.S. PATENT DOCUMENTS

| | | | |
|---|---|---|---|
| 2007/0093778 A1* | 4/2007 | Cindrich | A61M 5/158 |
| | | | 604/500 |
| 2008/0132833 A1* | 6/2008 | Harding | A61M 39/04 |
| | | | 604/93.01 |
| 2010/0168675 A1 | 7/2010 | Cindrich et al. | |
| 2011/0301541 A1* | 12/2011 | White | A61M 25/0637 |
| | | | 604/164.04 |
| 2012/0065612 A1 | 3/2012 | Stout et al. | |
| 2013/0218082 A1* | 8/2013 | Hyer | A61M 25/0097 |
| | | | 604/167.06 |

FOREIGN PATENT DOCUMENTS

| | | | |
|---|---|---|---|
| WO | 2002/096495 | 12/2002 | |
| WO | WO-02096495 A2 * | 12/2002 | ........ A61M 25/0606 |
| WO | 2007/050788 | 5/2007 | |
| WO | 2017/074677 | 5/2017 | |

* cited by examiner

LOW-DRAG SEPTUM FOR A CATHETER SYSTEM

RELATED APPLICATIONS

This application claims the benefit of U.S. Provisional Patent Application No. 62/722,041, filed on Aug. 23, 2018, entitled "LOW-DRAG SEPTUM FOR A CATHETER SYSTEM," which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing up away from skin of the patient. The PIVC and introducer needle are generally inserted at a shallow angle through the skin into vasculature of the patient.

In order to verify proper placement of the introducer needle and/or the PIVC in the vein, a user generally confirms that there is "flashback" of blood in a flashback chamber of a PIVC assembly. Once placement of the needle has been confirmed, a user may temporarily occlude flow in the vein and remove the introducer needle, leaving the PIVC in place within the vein. The user may also attach a device to the PIVC assembly for fluid infusion and/or blood withdrawal. This process has been somewhat difficult in practice since many PIVC placement sites simply do not allow easy occlusion of the vein. Additionally, even when such occlusion is achieved, it may be imperfect, resulting in blood leaking from the PIVC assembly housing the PIVC and endangering medical personnel.

PIVC assemblies have thus been provided in the art that provide a variety of seals or "septa" for preventing outflow of fluid during and following removal of the introducer needle from the vein. A septum may be secured within the PIVC assembly via friction and/or adhesive between the septum and a wall of the catheter assembly.

In some instances, after the PIVC has been placed within the vein, the introducer needle may be withdrawn from the PIVC assembly through the septum. The septum may significantly increase the force that the user needs to exert on the introducer needle in order to withdraw the introducer needle from the PIVC assembly. The force the user exerts may result in pain for the patient and/or dislodgement of the PIVC from the vein.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to septa for catheter assemblies, as well as related systems and methods. In some embodiments, a septum may reduce a drag force of an introducer needle that is moved with respect to the septum. In some embodiments, reducing the drag force may improve comfort of a patient and facilitate first stick success or placement of a catheter within the vein on a first try. In some embodiments, the drag force may be reduced by decreasing a surface area of the septum that contacts the introducer needle.

In some embodiments, a septum of a catheter assembly may include a body having a distal end and a proximal end. In some embodiments, the distal end of the body and the proximal end of the body may be sealed. In some embodiments, the septum may include a slot disposed within an outer surface of the body and oriented along a longitudinal axis of the body. In some embodiments, the slot may include a distal end spaced apart from the distal end of the body, and a proximal end spaced apart from the proximal end of the body. In some embodiments, the introducer needle may extend through the slot. In some embodiments, the introducer needle may be spaced apart from a bottom of the slot.

In some embodiments, the catheter assembly may include a catheter adapter and a catheter. In some embodiments, the catheter assembly may include PIVC catheter assembly having a PIVC. In some embodiments, the catheter assembly may include an integrated catheter system, having an integrated extension tube. In these and other embodiments, the septum, which may be disposed in the catheter adapter, may be configured for single use. In further detail, in some embodiments, the septum may be penetrated by the introducer needle when the catheter assembly is in an insertion position, but after the catheter is placed and the introducer needle is withdrawn through the septum, the septum may remain closed.

In some embodiments, an inner surface of the catheter adapter may seal the slot. In some embodiments, the catheter assembly may include a septum housing. In some embodiments, the septum may be at least partially disposed within the septum housing. In some embodiments, an inner surface of the septum housing may seal the slot.

In some embodiments, a length of the slot may correspond to a majority of a length of the body. In some embodiments, a depth of the slot may be greater than half a width of the body. In some embodiments, a bevel of the introducer needle may face upward and the slot may face downward. In some embodiments, the slot may face downward such that a droplet of blood disposed in the slot and from the introducer needle may be hidden from the patient. In some embodiments, the slot may be filled with a lubricant, which may reduce an appearance of the blood droplet to the patient and lower the drag force.

In some embodiments, the septum may include a semi-annular groove disposed within the body. In some embodiments, the semi-annular groove may facilitate securement of the septum within the catheter adapter. In some embodiments, the semi-annular groove may extend around a portion of a circumference of the body. In some embodiments, the slot may extend between a first end of the semi-annular groove and a second end of the semi-annular groove.

In some embodiments, the septum may include a channel, which may be disposed within the septum and oriented along a longitudinal axis of the body. In these and other embodiments, the septum may be monolithically formed as a single unit. In some embodiments, the channel may be formed by an inner surface of the body. In some embodiments, the introducer needle may extend through the channel. In some embodiments, the introducer needle may be spaced apart from the inner surface of the body. In some embodiments, at least a portion of the channel may be generally cylindrical. In some embodiments, a length of the channel may correspond to a majority of a length of the body.

In some embodiments, the septum may include a slit extending from an outer surface of the body to the channel. In some embodiments, the slit may be oriented along the longitudinal axis of the body. In some embodiments, the slit may be closed when the septum is disposed within the lumen of the catheter adapter. In some embodiments, the slit may extend through an entire length of the body. In some embodiments, the slit may extend partially through a length of the body.

In some embodiments, the septum may include the semi-annular groove or an annular groove, which may facilitate securement of the septum within the catheter adapter. In some embodiments, the slit may extend through the semi-annular groove or the annular groove. In some embodiments, the septum may be formed via injection molding. In some embodiments, the septum may be elastomeric. In some embodiments, the septum may be molded in a bulged position with the slit open to allow insertion of a mold and formation of the channel.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
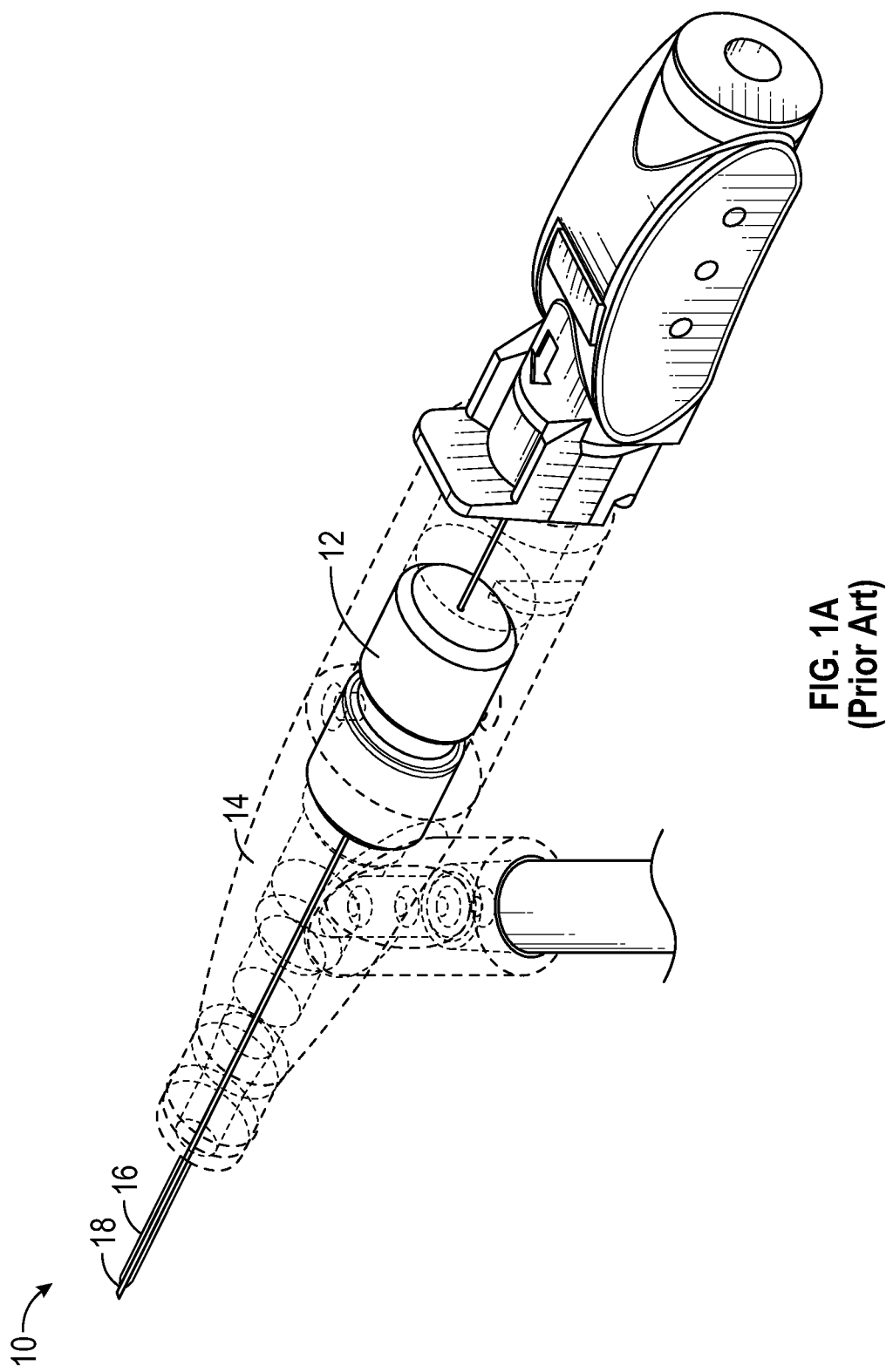
FIG. 1A is an upper perspective view of an example catheter assembly of the prior art.
Figure 1B:
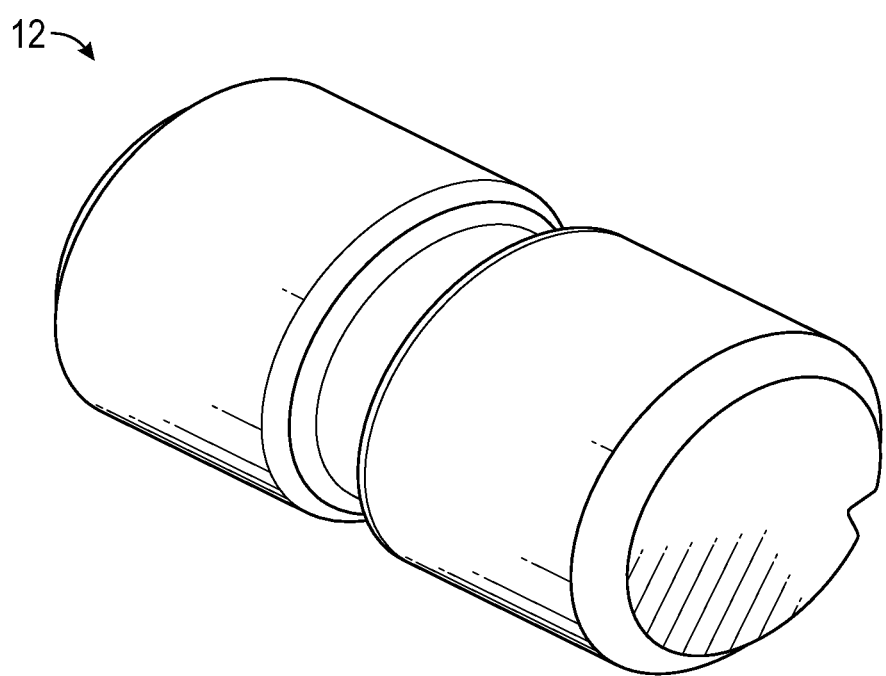
FIG. 1B is an upper perspective view of a septum of the prior art that may be used with the catheter assembly of FIG. 1A.
Figure 1C:
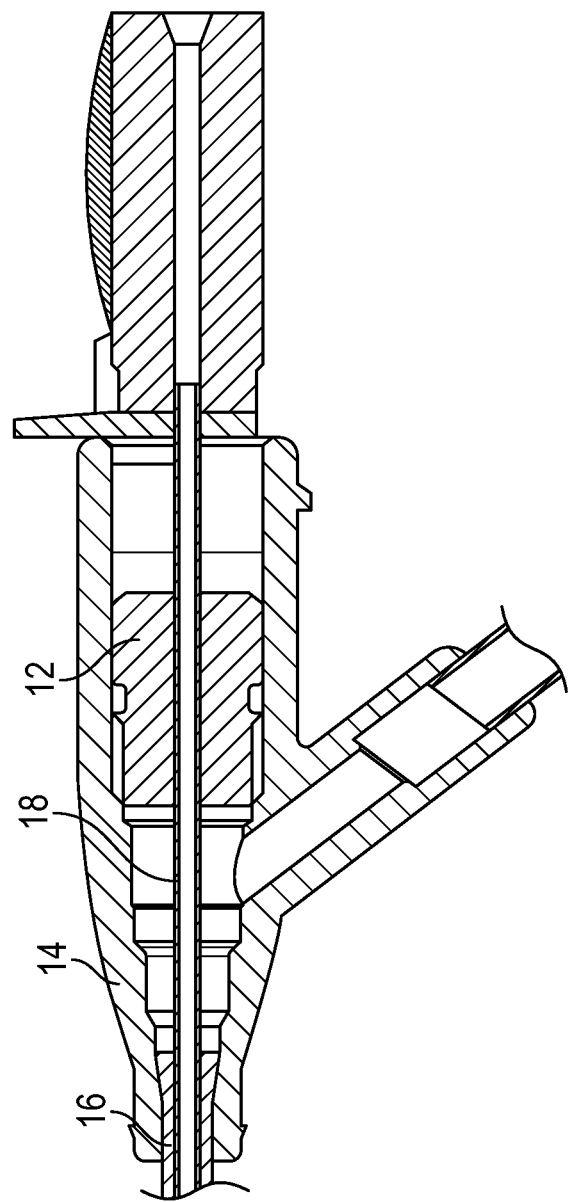
FIG. 1C is a cross-sectional view of the catheter assembly of FIG. 1A.

Referring now to FIG. 1A-1C, a catheter assembly 10 of the prior art is illustrated. The catheter assembly 10 may include a septum 12 disposed within a lumen of a catheter adapter 14 of the catheter assembly 10. A catheter 16 may extend distally from the catheter adapter 14. The septum 12 may correspond to the septum of the BD INTIMA II™ IV Catheter, for example. After a user confirms the catheter 16 of the catheter assembly 10 is positioned within a vein of a patient, an introducer needle 18 of the catheter assembly 10 may be withdrawn from the patient and the catheter assembly 10, leaving only the catheter 16 in place within the vein. As illustrated in FIG. 1C, an entire portion of the introducer needle 18 disposed within the septum 12 may contact the septum 12, creating a high drag force as the introducer needle 18 is withdrawn proximally from the patient and the catheter assembly 10. The high friction between the introducer needle 18 and the septum 12 may result in discomfort for the patient as the introducer needle 18 is withdrawn and/or dislodgement of the catheter 16 of the catheter assembly 10 from the vein of the patient.

Figure 2A:
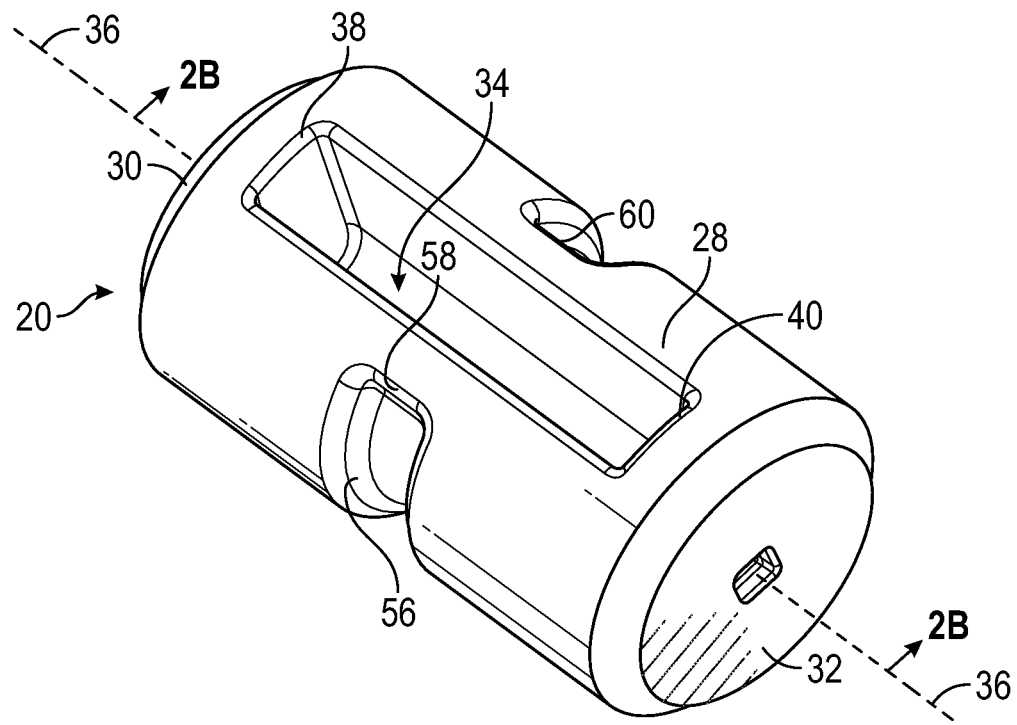
FIG. 2A is an upper perspective view of an example septum having a slot, according to some embodiments.
Figure 2B:
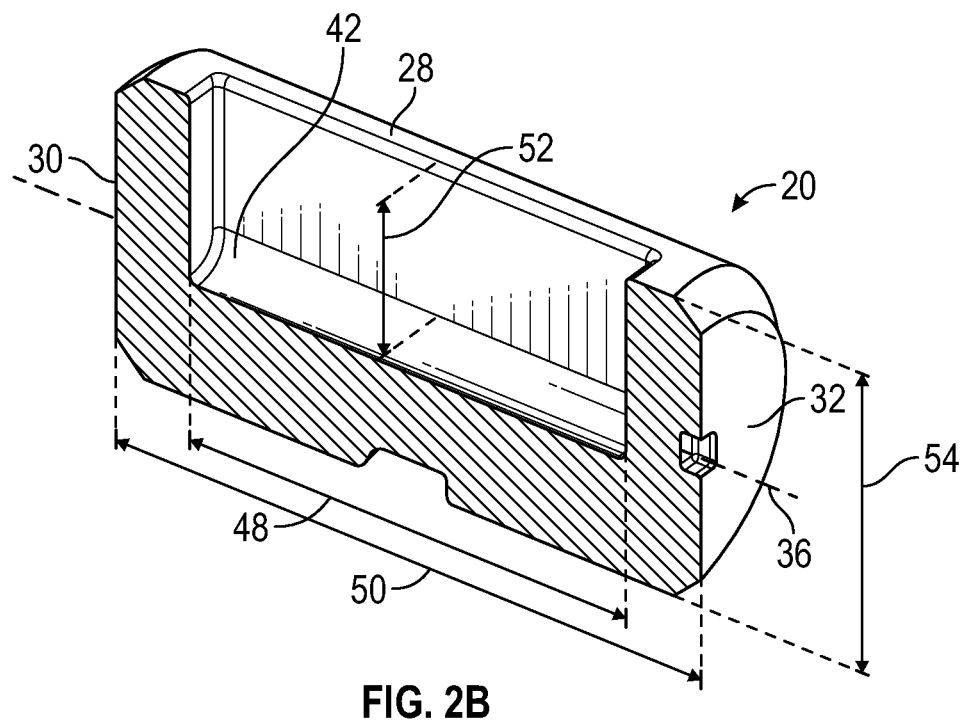
FIG. 2B is a cross-sectional view of the septum of FIG. 2A along the line 2B-2B, according to some embodiments.
Figure 2C:
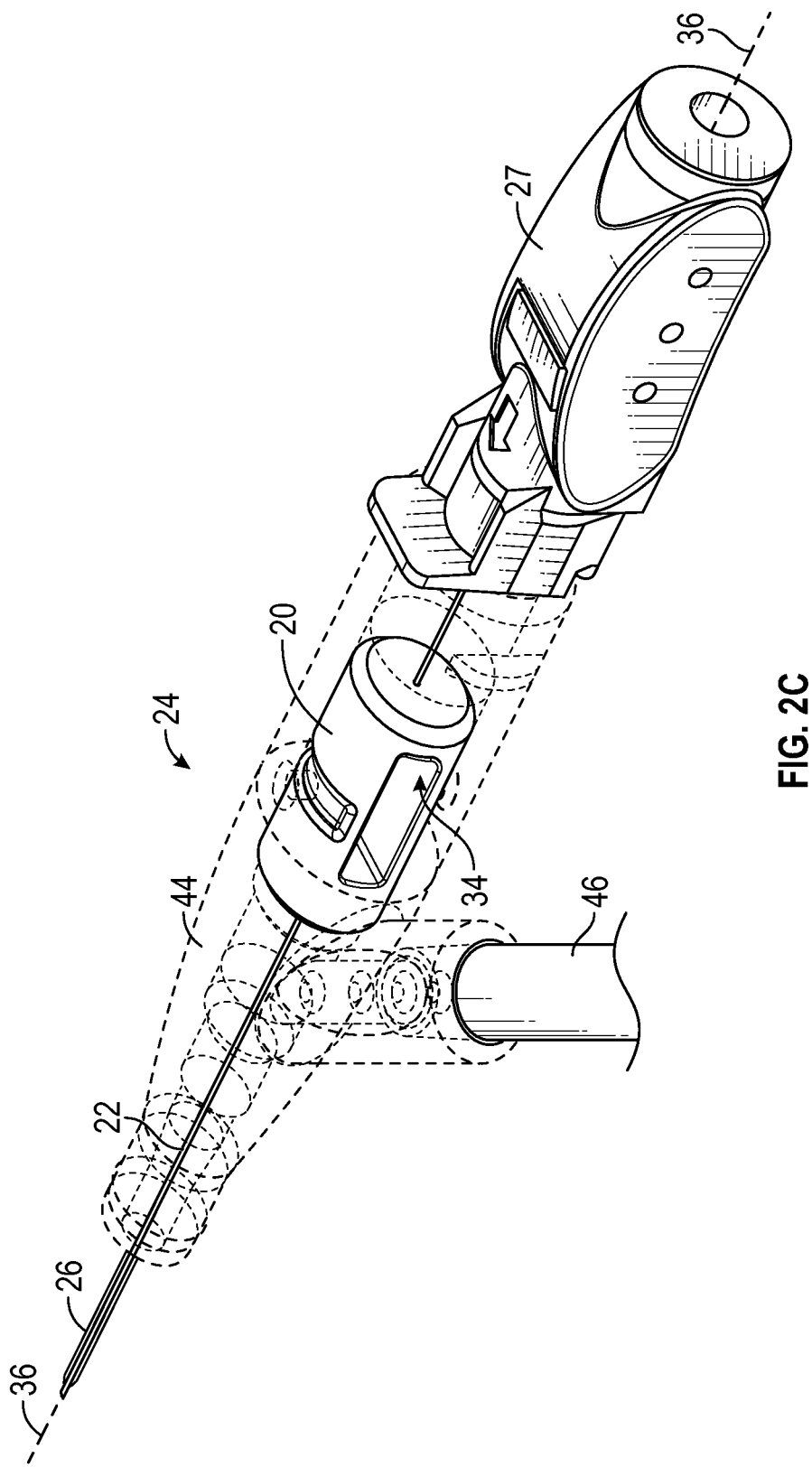
FIG. 2C is an upper perspective view of an example catheter assembly, illustrating the septum of FIG. 2A oriented in a first position, according to some embodiments.

Referring now to FIG. 2A-2C, in some embodiments, a septum 20 may reduce a drag force of an introducer needle 22 that is moved with respect to the septum 20 during withdrawal of the introducer needle 22 from the patient and a catheter assembly 24 in a proximal direction. In some embodiments, reducing the drag force may improve comfort of a patient and facilitate first stick success or placement of a catheter 26 within the vein on a first try. In some embodiments, the drag force may be reduced by decreasing a surface area of the septum 20 that contacts the introducer needle 22. In some embodiments, a proximal end of the introducer needle 22 may be secured in a needle hub 27.

In some embodiments, the septum 20 of the catheter assembly 24 may include a body 28 having a distal end 30 and a proximal end 32. In some embodiments, the distal end 30 of the body 28 and the proximal end 32 of the body 28 may be sealed. In some embodiments, the septum 20 may provide a seal about the introducer needle 18 during storage and use of the introducer needle 22, and then may seal the catheter assembly 24 when the introducer needle 22 is withdrawn to prevent escape of fluid. In some embodiments, the septum 20 may be pre-slit along the longitudinal axis 36 prior to insertion of the introducer needle 22 through the septum 20. In some embodiments, the septum 20 may not be pre-slit along the longitudinal axis 36.

In some embodiments, the distal end 30 of the body 28 may be disposed furthest away from the user of the catheter assembly 24 and nearest the patient to act as a primary seal and prevent escape of blood from the catheter assembly 24. In some embodiments, the proximal end 32 of the body 28 may act as a secondary seal to prevent escape of blood from the catheter assembly 24. In some embodiments, the distal end 30 and/or the proximal end 32 may wipe the introducer needle 22 as it is withdrawn. In some embodiments, the septum 20 may be constructed of an elastomeric or resilient material. In some embodiments, the septum 20 may be constructed of silicone and/or rubber. In some embodiments, the septum 20 may result in less material usage and cost savings. In some embodiments, the septum 20 may be monolithically formed as a single unit. In some embodiments, the septum 20 may include a one-piece or multi-piece septum.

In some embodiments, the septum 20 may include a slot 34 disposed within an outer surface of the body 28 and oriented along a longitudinal axis 36 of the body. In some embodiments, the slot 34 may include a distal end 38 spaced apart from the distal end 30 of the body 28, and a proximal end 40 spaced apart from the proximal end 32 of the body 28. In some embodiments, the introducer needle 22 may extend through the slot 34. In some embodiments, the introducer needle 22 may be spaced apart from a bottom 42 of the slot 34. In some embodiments, the slot 34 may reduce friction on the introducer needle 22. In some embodiments, the septum may only contact the introducer needle at the distal end 30 and the proximal end 32 of the body 28. In some embodiments, the slot 34 may have various shapes. In some embodiments, the slot 34 may be generally rectangular. In some embodiments, sides of the slot 34 disposed between the distal end 38 and the proximal end 40 may be straight, as illustrated, for example, in FIG. 2A, or another shape.

In some embodiments, the catheter assembly 24 may include a catheter adapter 44 and the catheter 26. In some embodiments, the catheter assembly 24 may include PIVC catheter assembly, and the catheter 26 may include a PIVC. In some embodiments, the catheter assembly 24 may include an integrated catheter system, having an integrated extension tube 46 extending from a side port of the catheter adapter 44. In these and other embodiments, the septum 20, which may be disposed in the catheter adapter 44, may be configured for single use. In further detail, in some embodiments, the introducer needle 22 may penetrate the septum 20 when the catheter assembly 24 is in an insertion position for insertion into the patient, but after the catheter 26 is placed within the vein and the introducer needle 22 is withdrawn proximally through the septum, the septum 20 may remain closed.

In some embodiments, a length 48 of the slot 34 may correspond to a majority of a length 50 of the body 28. In some embodiments, a depth 52 of the slot 34 may be greater than half a width 54 of the body 28, which may prevent a portion of the introducer needle 22 extending through the slot 34 from contacting the slot 34. In some embodiments, the septum 20 may be disposed in various orientations within the catheter adapter 44. FIG. 2C illustrates the septum 20 with the slot 34 facing a side of the catheter adapter 44, when the catheter assembly 24 is in the insertion position. In other embodiments, the slot 34 may face towards a top or bottom of the catheter adapter 44, when the catheter assembly 24 is in the insertion position. In some embodiments, an inner surface of the catheter adapter 44 may seal the slot 34.

In some embodiments, the septum 20 may include a groove 56, which may be semi-annular, disposed within the outer surface of the body 28. In some embodiments, the groove 56 may facilitate securement of the septum 20 within the catheter adapter 44. For example, the catheter adapter 44 may include a protrusion or similar element that fits within the groove 56. In some embodiments, the groove 56 may extend around a portion of a circumference of the body 28. In some embodiments, the slot 34 may extend between a first end 58 of the groove 56 and a second end 60 of the groove 56. In some embodiments, the septum 20 may be at least partially disposed in a septum housing.

Figure 2D:
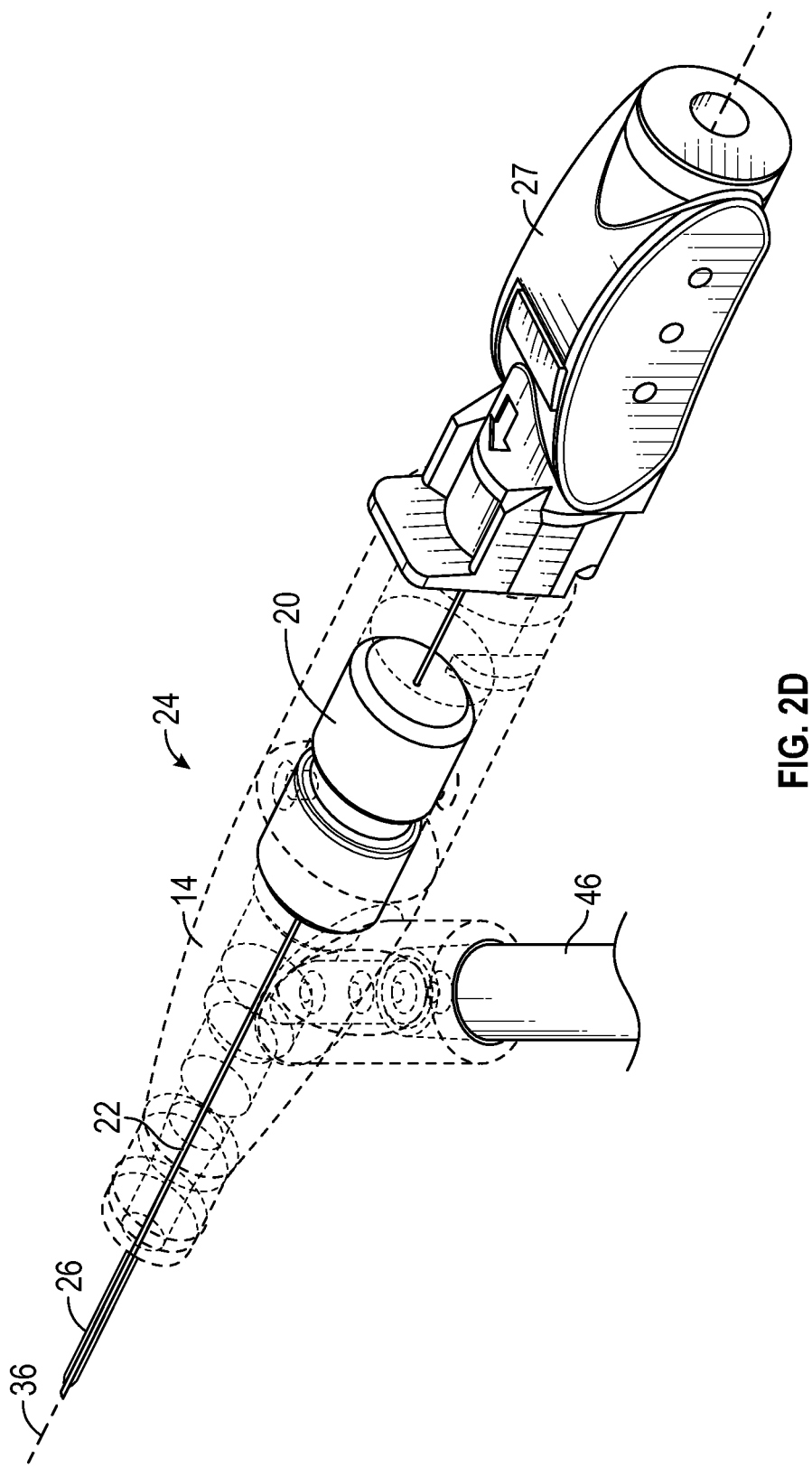
FIG. 2D is an upper perspective view of the catheter assembly, illustrating the septum of FIG. 2A oriented in a second position, according to some embodiments.
Figure 2E:
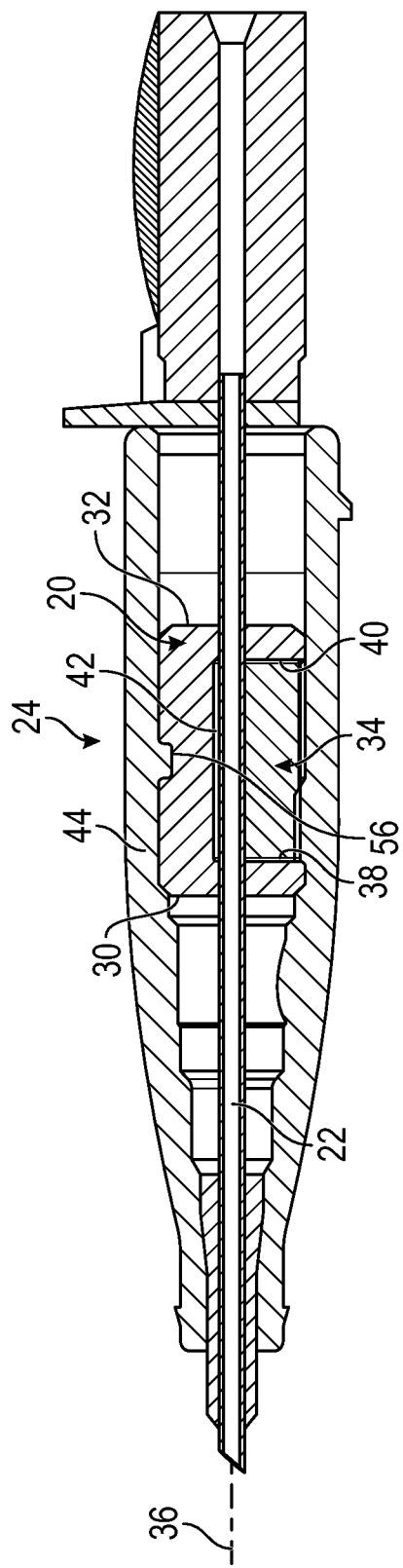
FIG. 2E is a cross-sectional view of the catheter assembly of FIG. 2D, according to some embodiments.

Referring now to FIG. 2D-2E, in some embodiments, in the insertion position, a bevel of the introducer needle 22 may face upward and the slot 34 may face downward or towards the bottom of the catheter adapter 44. In some embodiments, the slot 34 may face downward such that a droplet of blood disposed in the slot 34 and from the introducer needle 22 may be hidden from the patient, as illustrated, for example, in FIG. 2D-2E. In some embodiments, the slot 34 may be filled with a lubricant, which may reduce an appearance of the blood droplet to the patient and lower the drag force.

Figure 3A:
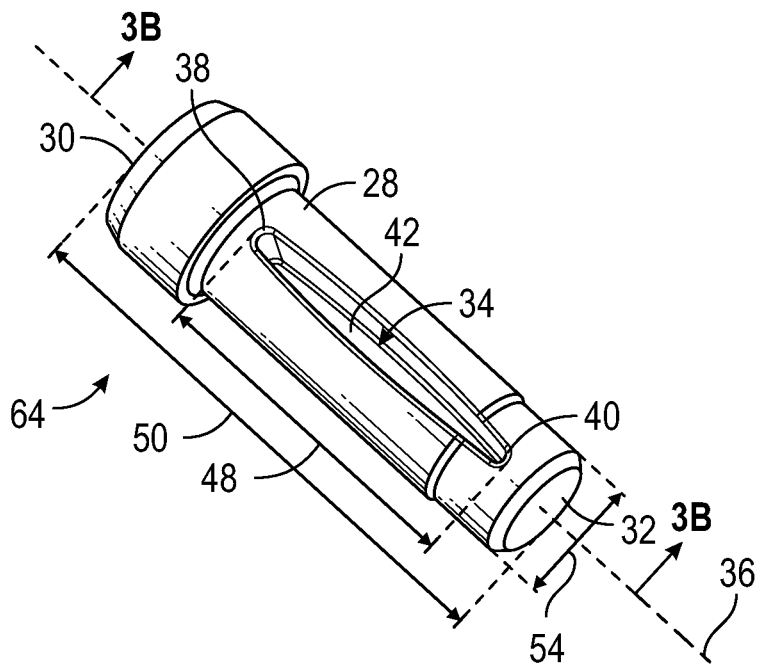
FIG. 3A is an upper perspective view of another example septum having a slot, according to some embodiments.
Figure 3B:
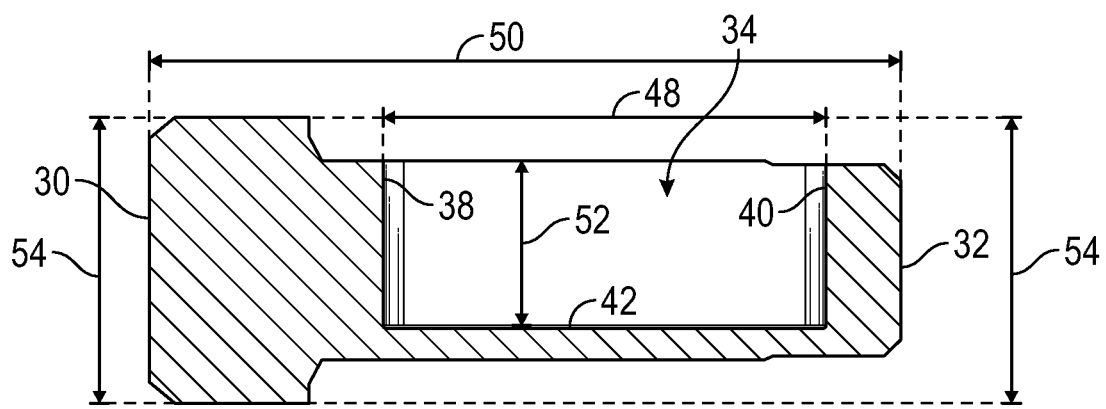
FIG. 3B is a cross-sectional view of the septum of FIG. 3A along the line 3B-3B, according to some embodiments.
Figure 3C:
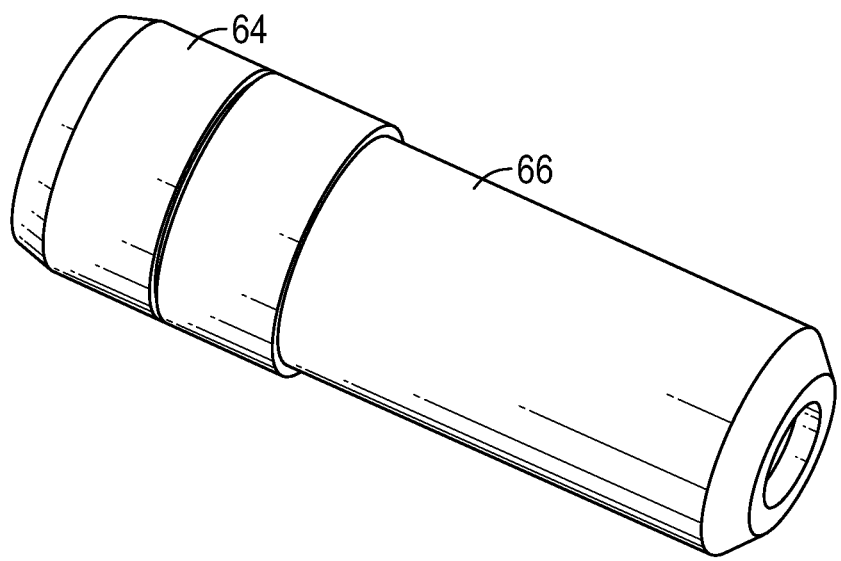
FIG. 3C is an upper perspective view of the septum of FIG. 3A disposed in an example septum housing, according to some embodiments.
Figure 3D:
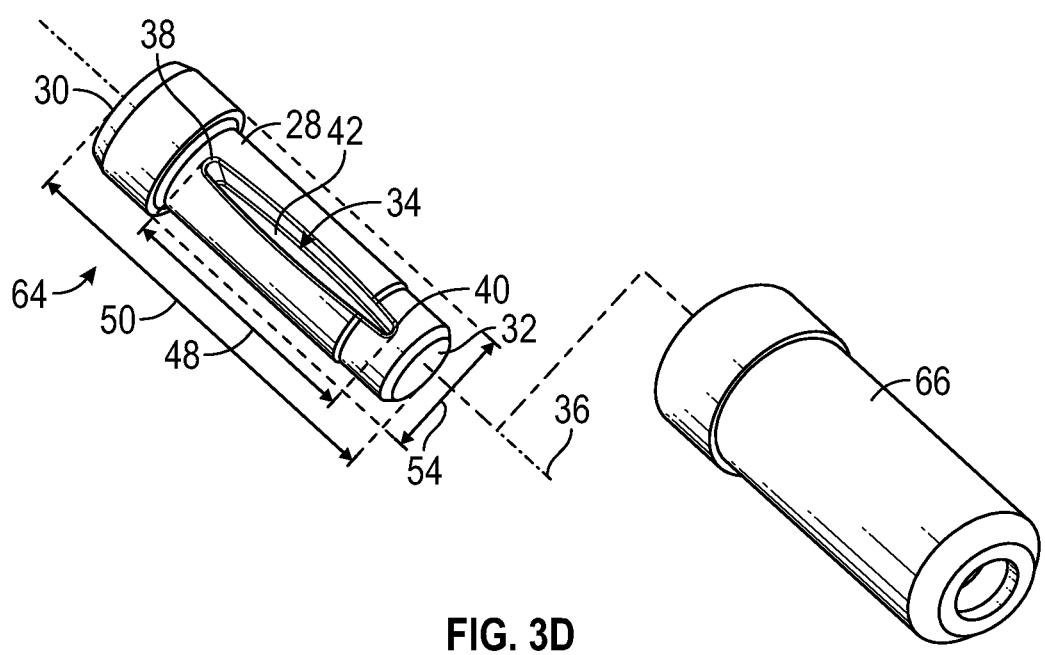
FIG. 3D is an exploded view of the septum and septum housing of FIG. 3C, according to some embodiments.

Referring now to FIG. 3A-3B, in some embodiments, a catheter assembly 62 may include a septum 64. In some embodiments, the catheter assembly 62 may include or correspond to the catheter assembly 24 of FIG. 2. In some embodiments, the catheter assembly 62 may include one or more features or elements of the catheter assembly 24. In some embodiments, the catheter assembly 24 may include one or more features or elements of the catheter assembly 62. In some embodiments, the septum 64 may include or correspond to the septum 20 of FIG. 2. In some embodiments, the septum 64 may include one or more features of the septum 20. In some embodiments, the septum 20 may include one or more features of the septum 64.

Figure 3E:
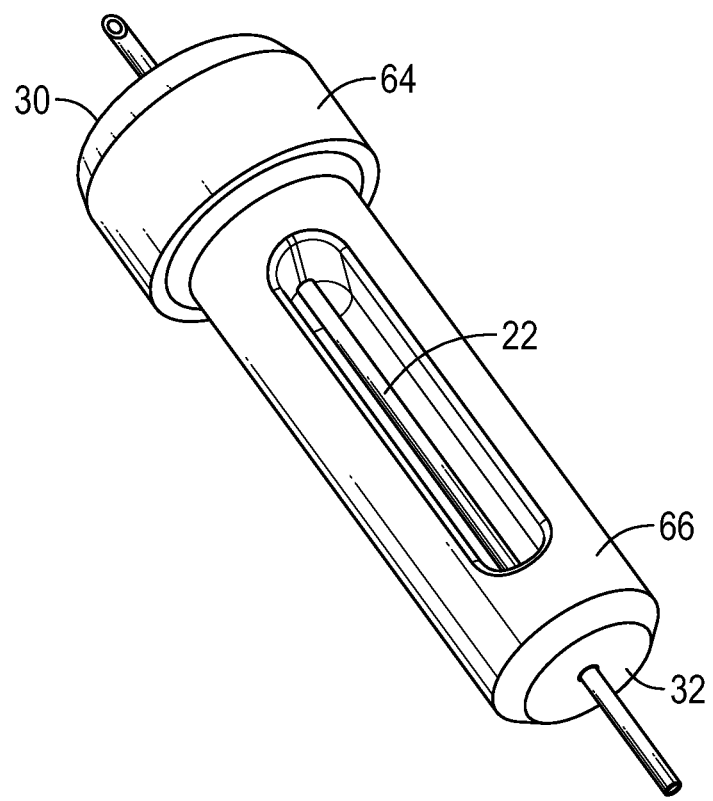
FIG. 3E is a partial cutaway view of the septum and septum housing of FIG. 3C, according to some embodiments.
Figure 3F:
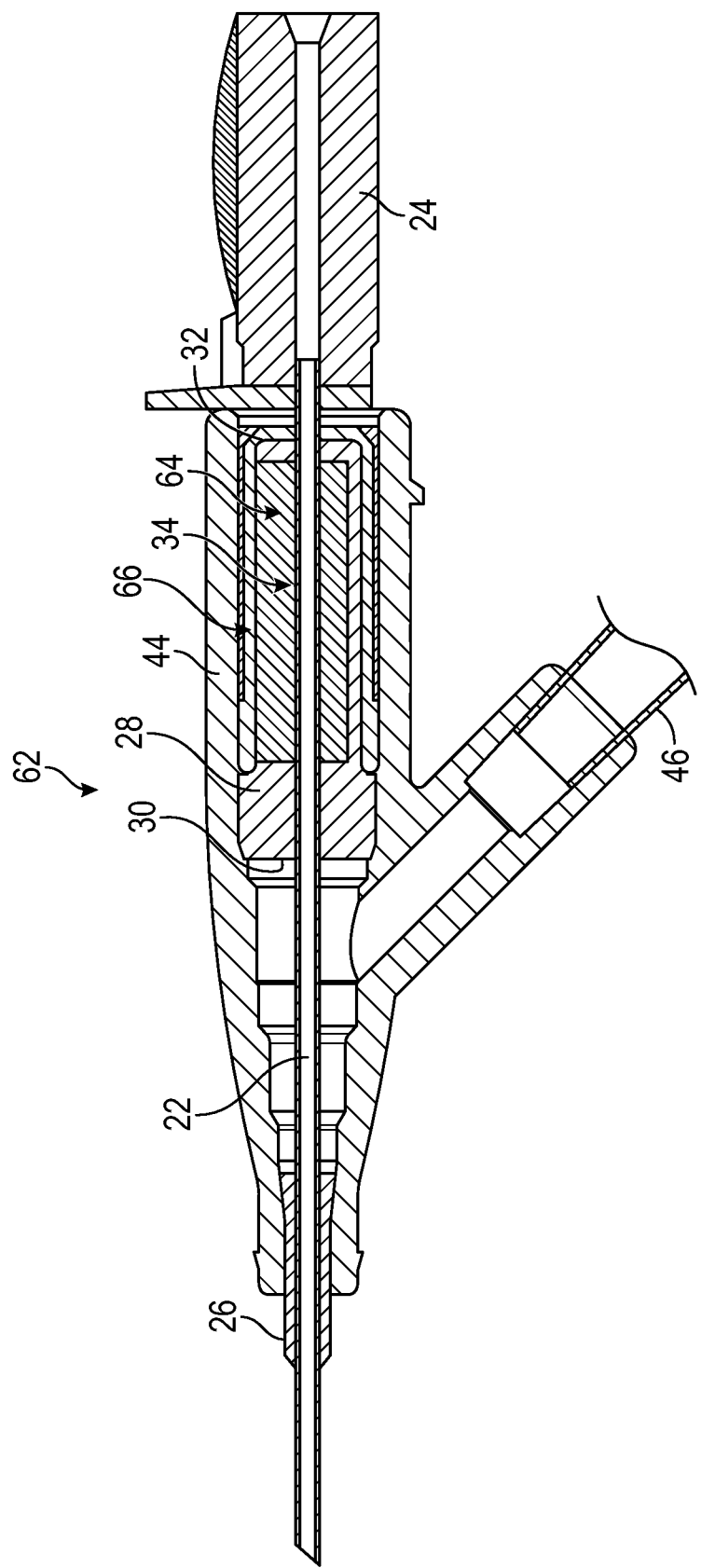
FIG. 3F is a cross-sectional view of the septum and septum housing of FIG. 3C in an example catheter assembly, according to some embodiments.
Figure 4A:
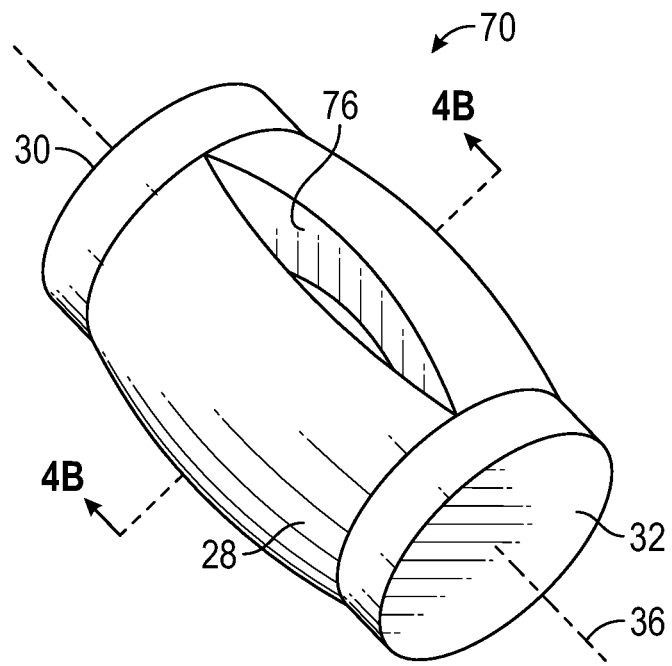
FIG. 4A is an upper perspective view of an example septum having a channel, according to some embodiments.
Figure 4B:
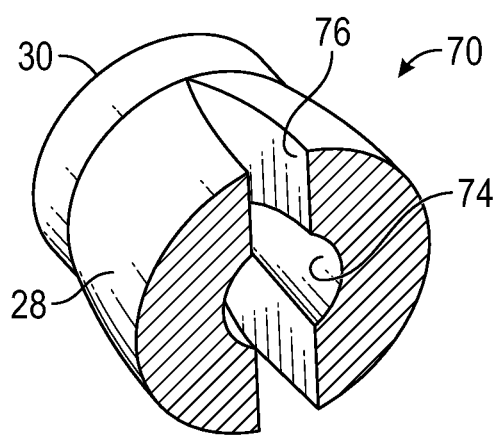
FIG. 4B is a cross-sectional view of the septum of FIG. 4A along the line 4B-4B, according to some embodiments.
Figure 4C:
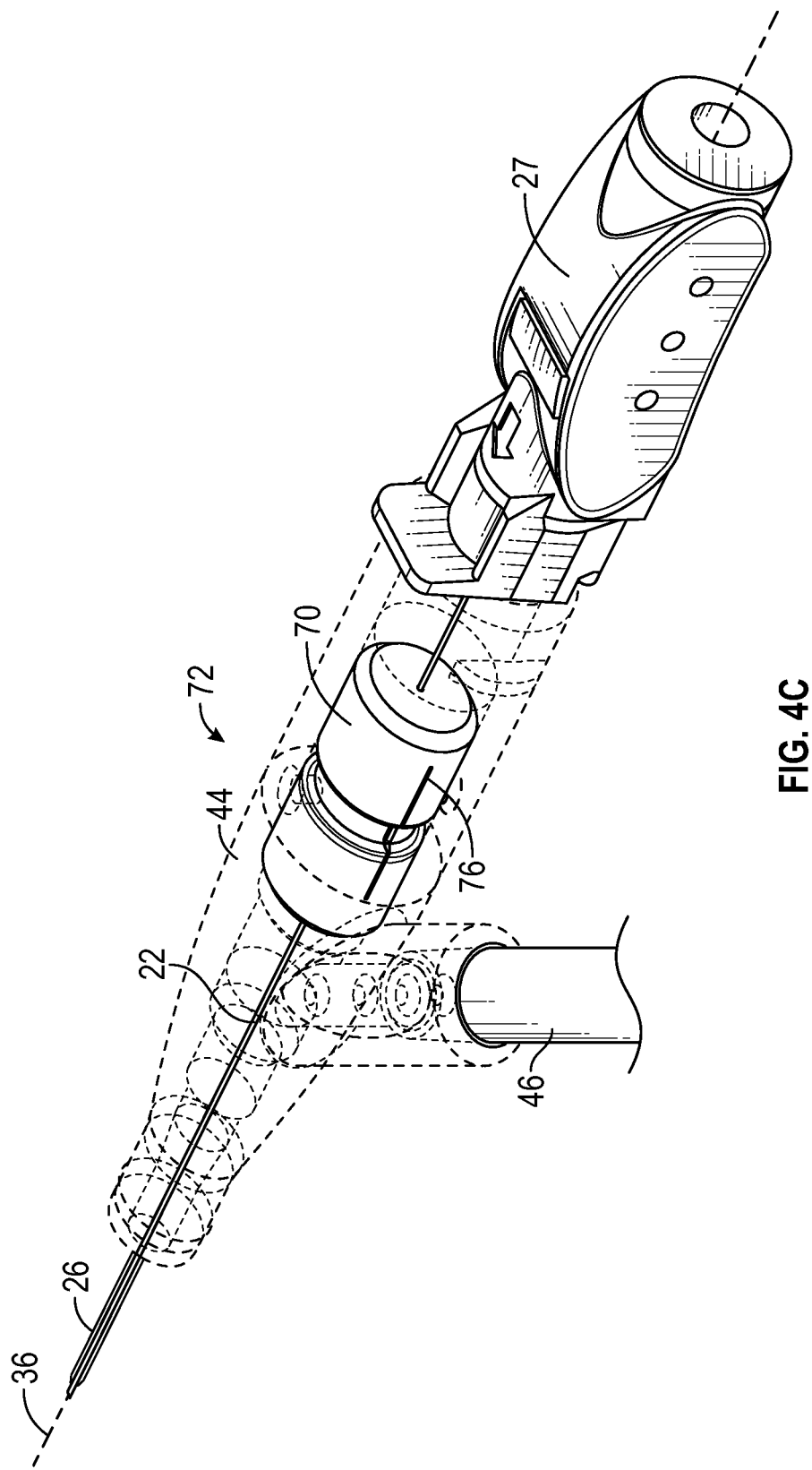
FIG. 4C is an upper perspective view of an example catheter assembly that includes the septum of FIG. 4A, according to some embodiments.
Figure 4D:
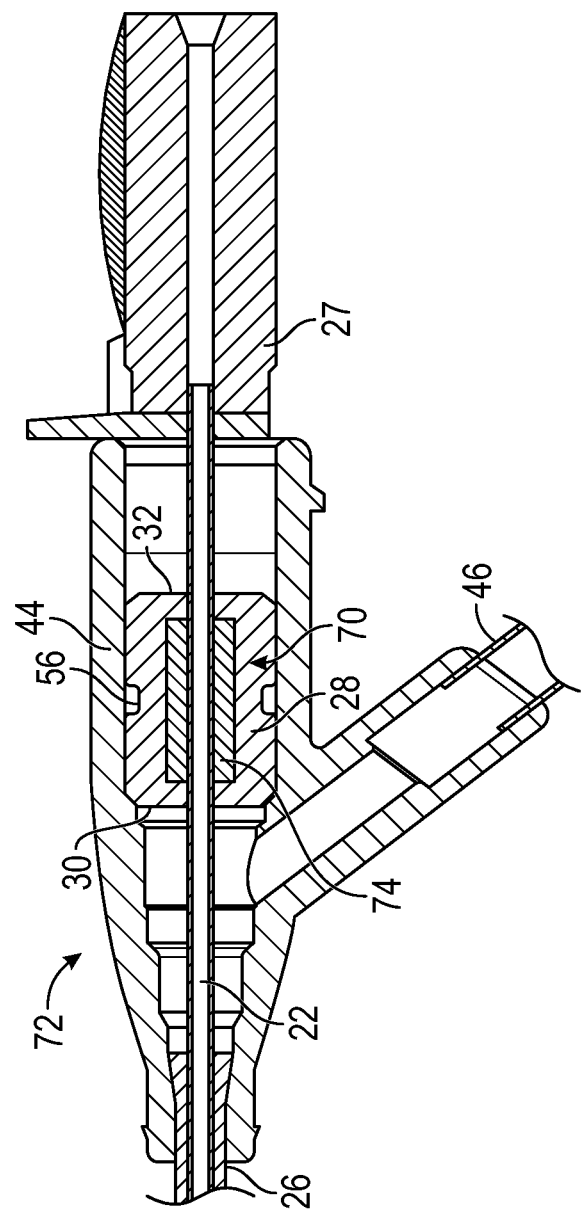
FIG. 4D is a cross-sectional view of the catheter assembly of FIG. 4C along the line 4D-4D, according to some embodiments.
Figure 5A:
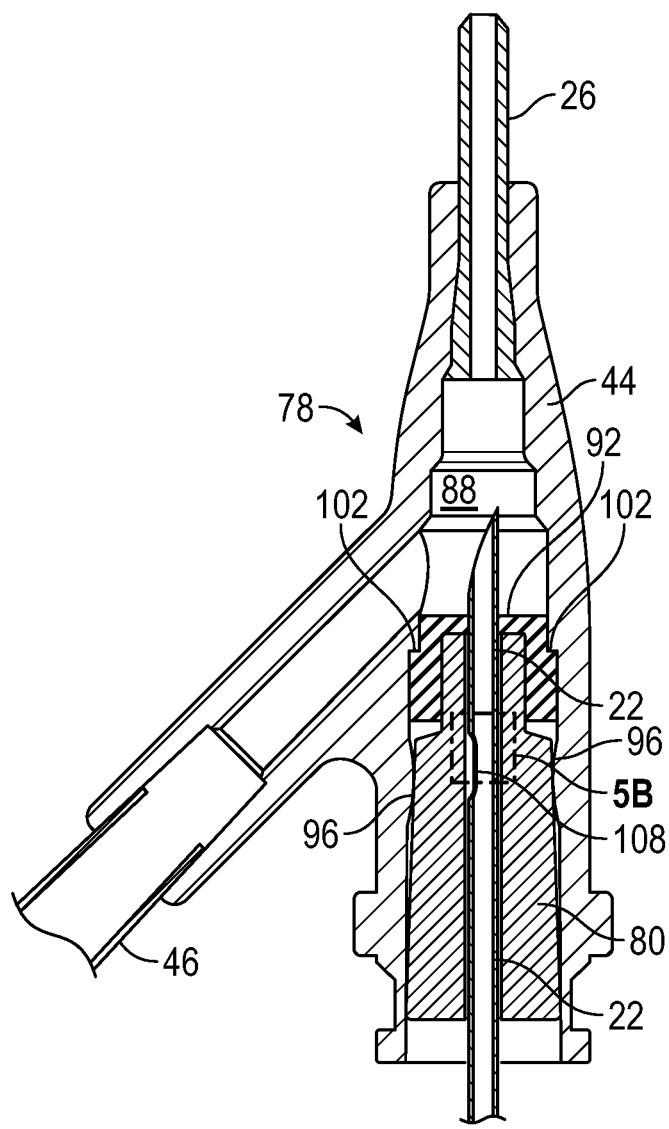
FIG. 5A is a cross-sectional view of another catheter assembly, illustrating an example introducer needle partially withdrawn, according to some embodiments.
Figure 5B:
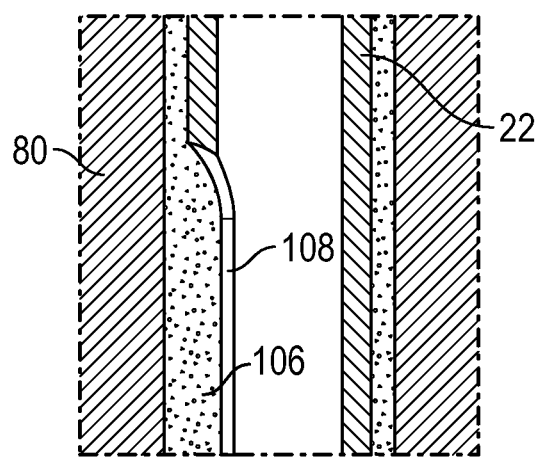
FIG. 5B is an enlarged view of a portion of the catheter assembly of FIG. 5A, according to some embodiments.
Figure 5C:
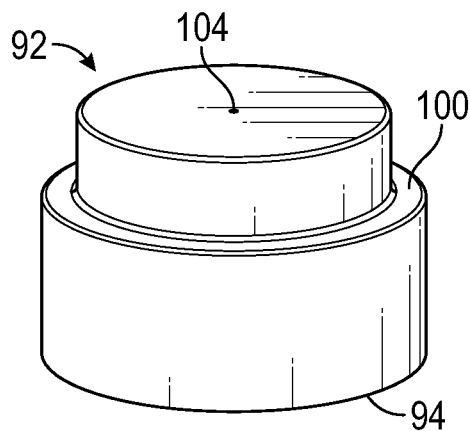
FIG. 5C is an upper perspective view of another example septum, according to some embodiments.
Figure 5D:
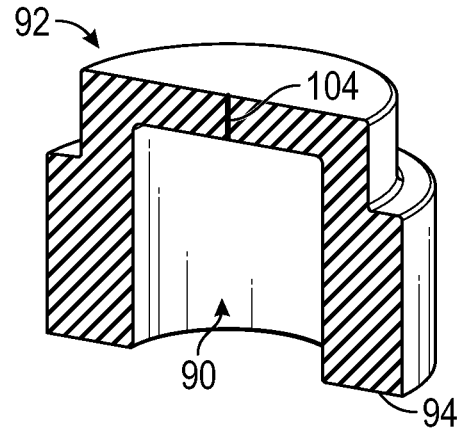
FIG. 5D is a cross-sectional view of the septum of FIG. 5C, according to some embodiments.
Figure 5E:
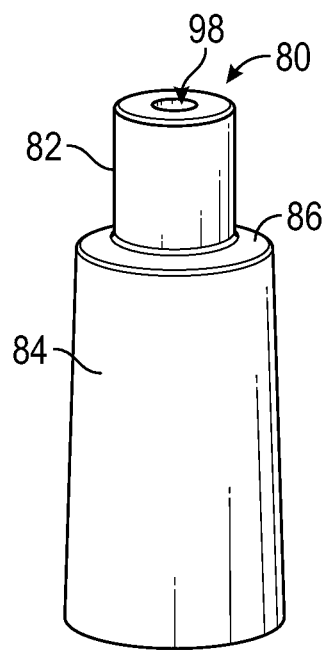
FIG. 5E is an upper perspective view of an example septum holder, according to some embodiments.
Figure 5F:
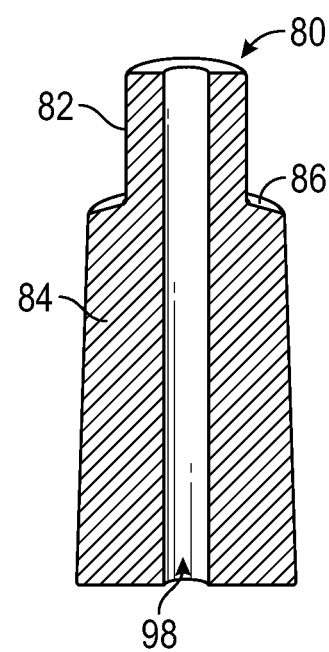
FIG. 5F is a cross-sectional view of the septum holder of FIG. 5E, according to some embodiments.

Referring now to FIGS. 3C-3F, in some embodiments, the septum 62 may be at least partially disposed within a septum housing 66. In some embodiments, an inner surface of the septum housing 66 may seal the slot 34 of the septum 62. In some embodiments, the septum housing 66 may provide compression to the septum 62. In some embodiments, the septum housing 66 may be a separate component or may instead be a region of the catheter adapter 44. In some embodiments, the septum housing 66 may include a canister that provides radial compression. In some embodiments, the radial compression from the canister helps to assure compliance of the septum 62 to the shape of the introducer needle 22 inserted there through and a tight seal upon withdrawal of the introducer needle 22. In some embodiments, the septum 62 may be held in place by compression alone, by a mechanical attachment or interlock, and/or by an adhesive as known to one of ordinary skill in the art. FIG. 3E illustrates the needle 22 partially withdrawn, according to some embodiments.

Referring now to FIGS. 4A-4D, in some embodiments, a septum 70 of a catheter assembly 72 may include a channel 74, which may be disposed within the septum 70 and oriented along the longitudinal axis 36 of the body 28. In some embodiments, the catheter assembly 72 may include or correspond to the catheter assembly 24 of FIG. 2 and/or the catheter assembly 62 of FIG. 3. In some embodiments, the catheter assembly 72 may include one or more features or elements of the catheter assembly 24 and/or the catheter assembly 62. In some embodiments, the catheter assembly 24 and/or the catheter assembly 62 may include one or more features or elements of the catheter assembly 72. In some embodiments, the septum 70 may include or correspond to the septum 20 of FIG. 2 and/or the septum 64 of FIG. 3. In some embodiments, the septum 20 and/or the septum 64 may include one or more features of the septum 70. In some embodiments, the septum 70 may include one or more features of the septum 20 and/or the septum 64.

In some embodiments, the septum 70 may be monolithically formed as a single unit. In some embodiments, the channel 74 may be formed by an inner surface of the body 28. In some embodiments, the introducer needle 22 may extend through the channel. In some embodiments, the introducer needle 22 may be spaced apart from the inner surface of the body 28. In some embodiments, at least a portion of the channel 74 may be generally cylindrical. In some embodiments, a distal end and/or a proximal end of the channel 72 may be tapered. In some embodiments, a length of the channel 74 may correspond to a majority of a length of the body 28.

In some embodiments, the septum 70 may include a slit 76 extending from an outer surface of the body 28 to the channel 74. In some embodiments, the slit 76 may be aligned with the longitudinal axis 36 of the body 28. In some embodiments, the slit 76 may be closed in response to the septum 70 being disposed within the lumen of the catheter adapter 44, which may compress the septum 70. In some embodiments, the slit 76 may extend through an entire length of the body 28. In some embodiments, the slit 76 may extend partially through a length of the body 28. In some embodiments, the slit 76 may be disposed in a middle of the body 28. In some embodiments, the septum 70 may or may not include the groove 56.

In some embodiments, the septum 70 may include the groove 56, which may be annular or semi-annular, which may facilitate securement of the septum 70 within the catheter adapter. In some embodiments, the slit 76 may extend through the groove 56. In some embodiments, the septum 70 may be formed via injection molding. In some embodiments, the septum 70 may be molded in a bulged position with the slit open to allow insertion of an undercut feature of a mold into the slit 76 and formation of the channel 74. In some embodiments, the elastomeric material of the septum 70 may allow the undercut feature to be removed from the channel 74 through the slit 76 following the injection molding.

Referring now to FIG. 5A-5F, another catheter assembly 78 is illustrated, according to some embodiments. In some embodiments, the catheter assembly 78 may include a septum holder 80, which may include a head 82 and a body 84. In some embodiments, an outer diameter of the head 82 may be less than an outer diameter of the body 84 such that an annular flange 86 is disposed between the head 82 and the body 84. In some embodiments, the head 82 may be disposed distal to the body 84 when the septum holder 80 is disposed within a lumen 88 of a catheter adapter 44. In some embodiments, the head 82 may be generally cylindrical. In some embodiments, the body 84 may be generally conical, having a tapered outer surface. In some embodiments, the outer surface of the body 84 may be tapered outwardly in a proximal direction.

In some embodiments, the head 82 may be sized and configured to fit snugly within a cavity 90 or pocket of a septum 92. In some embodiments, the cavity 90 may be cylindrical. In some embodiments, an outer diameter of the septum 92 may be slightly less than a diameter of the cavity 90. In some embodiments, the outer diameter of the septum 92 may be equal to or slightly greater than the diameter of the cavity 90, and the septum holder 80 may be in an interference fit with the septum 92. In some embodiments, a proximal end 94 of the septum 92 may contact the annular flange 86 of the septum holder 80. In some embodiments, the septum holder 80 and/or the catheter adapter 44 may be constructed of a plastic material or another suitable material.

In some embodiments, the septum holder 80 may facilitate securement of the septum 92 within the lumen 88 of the catheter adapter 44. In further detail, in some embodiments, an inner wall of the catheter adapter 44 forming the lumen 88 may include one or more protrusions 96 that may contact the outer surface of the body 84 to pinch the body 84 and hold the body 84 in place, thereby also securing the septum 92. In some embodiments, the protrusions 96 may be annular. In some embodiments, one or more sides of the protrusions 96 may include an undercut. In some embodiments, the protrusions 96 may include two opposing protrusions. In some embodiments, the protrusions 96 may be equally spaced or non-equally spaced around a circumference of the inner wall forming the lumen 88. In some embodiments, an outer diameter of the body 84 aligned with the protrusions 96 may be greater than a distance between the protrusions 96 to facilitate the pinching action.

In some embodiments, the septum 92 and the septum holder 80 may reduce drag on the introducer needle 22 as the introducer needle 22 is withdrawn in the proximal direction. In further detail, the septum holder 80 may allow a reduced area of the septum 92 that the introducer needle 22 passes through and contacts. In some embodiments, the septum holder 80 may include a passageway 98 extending through the septum holder 80. In some embodiments, when the catheter assembly 78 is in the insertion position and/or the introducer needle 22 is being withdrawn, the introducer needle 22 may extend through the passageway 98 and/or be spaced apart from a wall of the passageway 98 along all or a portion of a length of the passageway 98. In some embodiments, a portion of the introducer needle 22 disposed within the passageway 98 may be surrounded by an annular space. In some embodiments, an outer diameter of the introducer needle 22 may be less than a diameter of the passageway 98. In some embodiments, there may not be any contact between the wall forming the passageway 98 and the introducer needle 22.

In some embodiments, the septum 92 may include a flange 100, which may contact one or more corresponding flanges 102 of the catheter adapter 44, which may facilitate securement of the septum 92. In some embodiments, the corresponding flanges 102 of the catheter adapter 44 may prevent distal movement of the septum 92, and the septum holder 80 may prevent proximal movement of the septum 92. In some embodiments, one or more of the following may facilitate securement of the septum 92 within the lumen 88, which may strengthen a liquid seal of the septum 92: contact or interference between the flange 100 and the corresponding flange 102, contact or interference between the head 82 of the septum holder 80 and the septum 92, and contact or interference between the body 84 of the septum holder 80 and the protrusions 96.

In some embodiments, the distal end 30 of the septum 92 may be flush or near flush with a y-channel of the catheter adapter 44, which may facilitate flushability and reduction of dead space for blood. In some embodiments, the distal end 30 of the septum 92 may include a slit 104. In some embodiments, the septum 92 may be pre-slit or the slit 104 may be formed by the introducer needle 22 during assembly. In some embodiments, all or a portion of the slit 104 may be coated with a hydrophobic coating, such as, for example, parylene or another suitable hydrophobic coating. In some embodiments, the hydrophobic coating may decrease a coefficient of friction as the introducer needle 22 is withdrawn proximally from the catheter assembly 78. In some embodiments, a combination of the hydrophobic coating disposed within the slit 104 and a reduced contact area of the introducer needle 22 with the septum 92, may reduce the drag force on the introducer needle 22 as the introducer needle 22 is withdrawn proximally from the catheter assembly 98.

In some embodiments, all or a portion of the wall of the passageway 98 may be coated with a high-viscosity lube 106, which may be non-migrating. In some embodiments, the high-viscosity lube 106 may be applied to a proximal end of the passageway 98. In some embodiments, the high-viscosity lube 106 may at least partially block and cover a notch 108 of the introducer needle 22 as the introducer needle 22 is being withdrawn, which may prevent leakage of blood. In some embodiments, the high-viscosity lube 106 may reduce drag as the introducer needle 22 is withdrawn proximally from the catheter assembly 78.

It is understood that in some embodiments, the catheter assembly 78 may include or correspond to one or more of the following: the catheter assembly 24 of FIG. 2, the catheter assembly 62 of FIG. 3, or the catheter assembly 72 of FIG. 4. In some embodiments, the catheter assembly 78 may include one or more features or elements of one or more of the following: the catheter assembly 24, the catheter assembly 62, and the catheter assembly 72. For example, in some embodiments, the septum 92 may include or correspond to one or more of the following: the septum 20 of FIG. 2, the septum 64 of FIG. 3, and the septum 70 of FIG. 4. In some embodiments, one or more of the following may include one or more features or elements of the catheter assembly 78: the catheter assembly 24, the catheter assembly 62, and the catheter assembly 72.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A peripheral intravenous catheter assembly, comprising:
 a septum, comprising:
  a body having a distal end and a proximal end, wherein the distal and proximal ends of the body are sealed; and
  a slot disposed within an outer surface of the body and oriented along a longitudinal axis of the body, wherein the slot comprises a distal end spaced apart from the distal end of the body, and a proximal end spaced apart from the proximal end of the body, wherein the septum is monolithic; and
  a semi-annular groove disposed within the body, wherein the semi-annular groove extends around a portion of a circumference of the body, wherein the slot extends between a first end of the semi-annular groove and a second end of the semi-annular groove; and
 an introducer needle extending through the slot.

2. The peripheral intravenous catheter assembly of claim 1, wherein the introducer needle is spaced apart from a bottom of the slot.

3. The peripheral intravenous catheter assembly of claim 1, further comprising a catheter adapter, wherein the septum is disposed within the catheter adapter, wherein an inner surface of the catheter adapter seals the slot.

4. The peripheral intravenous catheter assembly of claim 3, wherein the catheter adapter comprises a side port having an integrated extension tube.

5. The peripheral intravenous catheter assembly of claim 1, further comprising a septum housing, wherein the septum is at least partially disposed within the septum housing, wherein an inner surface of the septum housing seals the slot.

6. The peripheral intravenous catheter assembly of claim 1, wherein the septum is elastomeric.

7. The peripheral intravenous catheter assembly of claim 1, wherein a length of the slot corresponds to a majority of a length of the body.

8. The peripheral intravenous catheter assembly of claim 1, wherein a depth of the slot is greater than half a width of the body.

9. The peripheral intravenous catheter assembly of claim 1, wherein a bevel of the introducer needle faces upward, wherein the slot faces downward.

10. The peripheral intravenous catheter assembly of claim 1, wherein the distal end of the slot is opposite the proximal end of the slot, wherein the slot further comprises a first sidewall and a second sidewall opposite the first sidewall, wherein the first sidewall and the second sidewall extend from the distal end of the slot to the proximal end of the slot, wherein the distal end, the proximal end, the first sidewall, and the second sidewall are monolithically formed of an elastomeric material as a single unit.

11. A peripheral intravenous catheter assembly, comprising:
 a catheter adapter;
 a septum, comprising:
  a body having a distal end and a proximal end, wherein the distal and proximal ends of the body are sealed; and
  a slot disposed within an outer surface of the body and oriented along a longitudinal axis of the body, wherein the slot comprises a distal end spaced apart from the distal end of the body, and a proximal end spaced apart from the proximal end of the body; and
 an introducer needle extending through the slot; and
 a semi-annular groove disposed within the body, wherein the semi-annular groove extends around a portion of a circumference of the body, wherein the slot extends between a first end of the semi-annular groove and a second end of the semi-annular groove; and
 a septum housing, wherein the septum is disposed within the septum housing, the septum housing encircling the septum and sealing the slot; wherein the septum housing is disposed within the catheter adapter.

12. The peripheral intravenous catheter assembly of claim 11, wherein the introducer needle is spaced apart from a bottom of the slot.

13. The peripheral intravenous catheter assembly of claim 11, wherein a bevel of the introducer needle faces upward, wherein the slot faces downward.

14. The peripheral intravenous catheter assembly of claim 11, wherein the septum is elastomeric.

15. The peripheral intravenous catheter assembly of claim 11, wherein a length of the slot corresponds to a majority of a length of the body.

16. The peripheral intravenous catheter assembly of claim 11, wherein a depth of the slot is greater than half a width of the body.

17. The peripheral intravenous catheter assembly of claim 11, wherein the catheter adapter comprises a side port having an integrated extension tube.

* * * * *